(12) United States Patent
Taylor

(10) Patent No.: US 7,759,110 B2
(45) Date of Patent: Jul. 20, 2010

(54) PROCESS FOR THE PRODUCTION OF (S)-5-CHLORO-2-ISOPROPYLPENT-4-ENOIC ACID ESTERS

(76) Inventor: Ian N. Taylor, 3 Henley Way, Ely, Cambs CB& 4YH (GB)

( * ) Notice: Subject to any disclaimer, the term of this patent is extended or adjusted under 35 U.S.C. 154(b) by 243 days.

(21) Appl. No.: 11/659,781

(22) PCT Filed: Jul. 28, 2005

(86) PCT No.: PCT/US2005/027122

§ 371 (c)(1), (2), (4) Date: Sep. 13, 2007

(87) PCT Pub. No.: WO2006/033705

PCT Pub. Date: Mar. 30, 2006

(65) Prior Publication Data

US 2008/0131944 A1 Jun. 5, 2008

(30) Foreign Application Priority Data

Aug. 11, 2004 (EP) .................................. 04254828

(51) Int. Cl.
*C12P 41/00* (2006.01)
*C12P 7/62* (2006.01)

(52) U.S. Cl. ...................... 435/280; 435/135

(58) Field of Classification Search .................. None
See application file for complete search history.

(56) References Cited

U.S. PATENT DOCUMENTS

| | | | | |
|---|---|---|---|---|
| 5,244,803 A * | 9/1993 | Mori et al. | ................... | 435/280 |
| 5,869,309 A | 2/1999 | Politino et al. | | |
| 5,912,164 A * | 6/1999 | Warneck et al. | ............. | 435/280 |
| 6,777,574 B1 | 8/2004 | Herold et al. | | |
| 7,232,925 B2 * | 6/2007 | Mori et al. | ................... | 560/219 |

2005/0228193 A1 10/2005 Mori et al.

FOREIGN PATENT DOCUMENTS

| WO | WO 94/20633 | 9/1994 |
|---|---|---|
| WO | WO 99/04015 | 1/1999 |
| WO | WO 02/092828 | 11/2002 |
| WO | WO 2004/055177 | 7/2004 |

OTHER PUBLICATIONS

Michael Politino et al., "Purification and Characterization of a Cephalosporin Esterase from *Rhodoporidium toruloides*", Applied and Environmental Microbiology, vol. 63, No. 12, Dec. 1997, pp. 4807-4811.
Dondoni et al., Tetrahedron Lett., 41 (2001), 4819-4823.

* cited by examiner

*Primary Examiner*—Herbert J. Lilling

(57) ABSTRACT

A process for preparing a compound of formula (1) in enantiomerically enriched form, which comprises selective hydrolysis of the corresponding racemic compound (2) catalysed by an enzyme derived from a non-mammalian source and having esterase or lipase activity, wherein R is methyl or $C_{2-10}$ linear or branched alkyl. The non-mammalian source is a preferably yeast from the genus *Rhodosporidium*, preferably *Rhodosporidium toruloides*, in particular *Rhodosporidium toruloides* CMC 103105 or CMC 103107

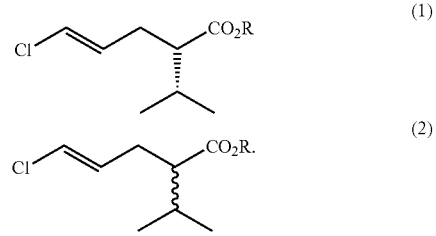

17 Claims, No Drawings

PROCESS FOR THE PRODUCTION OF (S)-5-CHLORO-2-ISOPROPYLPENT-4-ENOIC ACID ESTERS

CROSS REFERENCE TO RELATED APPLICATIONS

This application is a 371 of PCT/US2005/07122 filed 28 Jul. 2005, which claims the benefit of European Application No. 04254828.9, filed 11 Aug. 2004.

FIELD OF THE INVENTION

The invention relates to the production of (S)-5-chloro-2-isopropylpent-4-enoic acid esters, in particular, the methyl ester, which is a key intermediate in the manufacture of the drug Aliskiren.

BACKGROUND TO THE INVENTION

Aliskiren is a renin inhibitor which is under development for the treatment of several cardiovascular indications including congestive heart failure, hypertension and chronic renal failure. The renin-angiotensin cascade is one of the key regulators of electrolyte and fluid balance and blood pressure. Currently available drugs, including ACE inhibitors (angiotensin converting enzyme) are antagonists of the latter parts of this cascade. Aliskiren, the first of a new class of peptidomimetics, offers potential as a more selective inhibitor through action in the first half of the pathway.

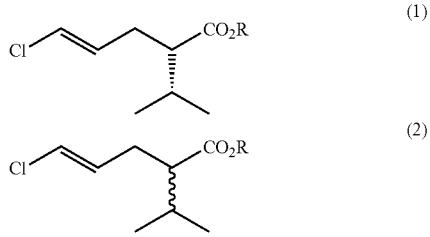

Aliskiren, also known as SPP-100, can be synthesised through the addition of a Grignard reagent derived from a 3-aryl-2-isopropyl-1-chloropropane to the nitrone function of a pseudoephidrine spiroanellated gamma-butyrolactone (Dondoni et al., Tetrahedron Lett., 42 (2001), 4819-4823). A more efficient synthesis, described in WO 01/09079 and WO 02/092828 proceeds via an (S)-5-chloro-2-isopropylpent-4-enoic-acid alkyl ester (1). An ester of formula (1) can be obtained in enantiomerically enriched form by hydrolysis of corresponding racemic ester to form the carboxylic acid, followed by racemate separation by means of diastereomeric salt formation with chiral amine bases and crystallization, followed by re-esterification. A stereoselective synthesis utilising chiral auxiliaries is further described for the preparation of such 2(S)-pentenoic acids and their derivatization to form the corresponding carboxylic acid halides, esters and amides. This stereoselective synthesis of the esters is not yet satisfactory and is regarded as too costly. WO 02/092828 describes how an ester of formula (1) can be obtained preferentially, by bioresolution of the racemic carboxylic ester (2) using a mammalian esterase, namely Pig liver esterase (PLE). Although from a technical perspective this provides an efficient process, for the reasons set out below use of a mammalian esterase in commercial production of the key intermediate (1) is not favoured. Furthermore, to overcome to this problem, it is normally very difficult to identify suitable non-mammalian alternatives to mammalian enzymes that provide equivalent catalysis for such preparative bioresolution processes.

There are a number of reasons that the use of animal derived products in the synthesis of pharmaceutical intermediates is commercially unattractive. Principal among these is the fact that they are becoming subject to increasingly stringent regulatory guidance. The "note for guidance on minimizing the risk of transmitting spongiform encephalopathy agents via human and vetinary medicinal products" (EMEA/410/01/01 Rev2 October 2003) became enforceable as of 1 Jul. 2004 The driving force behind such scrutiny is the increasing incidence of previously unidentified emergent diseases such as the transmissible spongiform encephalopathy responsible for BSE (bovine spongiform encephalopathy). Such emergences, like the virus causing SARS (Severe Acute Respiratory Syndrome) arising from organisms jumping the cross species barrier are also a cause for future concern. In such cases, and other highly infectious animal diseases, for example, Foot and Mouth disease, quarantine and mass culling of animals has resulted, and this could have serious impact upon the supply of materials derived from animals susceptible to infection. In response, many pharmaceutical companies are taking pre-emptive action and require processes for manufacture of active pharmaceutical ingredients (APIs) and their registered starting materials to be developed without animal products. This mitigates the risk of later being held responsible for any prevailing patient infections and moreover protects the supply chain of raw materials used in the manufacture of APIs.

For investigation of enantioselective hydrolysis processes for carboxylic esters, the range of commercially available esterases is limited. Most come from animal origin, for example, pig liver esterase (PLE). Attempts have recently been reported to produce recombinant PLE in a heterologous bacterial host (WO2004/055177). However, since the selectivity of native PLE preparations may derive from a particular combination of isoforms present in the animal derived product, such artificial esterases may not always have the desired selectivity for a given reaction.

Politino et al. (Appl Environ Microbiol. 1997 63(12):4807-11; U.S. Pat. No. 5,869,309) describe the use of *Rhodosporidium toruloides* as a source of a cephalosporin esterase, having utility in the hydrolysis of the 3'-acetyl group of certain cephalosporins.

SUMMARY OF THE INVENTION

The present invention provides a novel process to prepare a compound of formula (1) in enantiomerically enriched form, which process comprises selectively hydrolyzing the corresponding racemic compound (2) catalysed by an enzyme derived from a non-mammalian source and having esterase or lipase activity, wherein R is methyl or $C_{2-10}$ linear or branched alkyl. Compound (1) is a key intermediate in the manufacture of the drug Aliskiren.

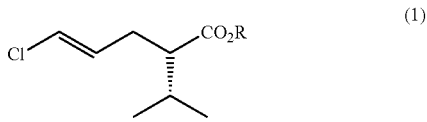

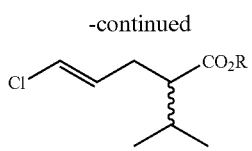

(2)

DESCRIPTION OF THE INVENTION

In the compounds of formulae (1) and (2), R is methyl or $C_{2-10}$ linear or branched alkyl, preferably methyl or $C_{2-6}$ linear alkyl. More preferably, R is methyl and most preferably R is methyl. The bioresolution process of the present invention can be carried out according to one of two protocols. Preferably, the enzyme hydrolyses the opposite enantiomer of compound (1) selectively, and unreacted compound (1) is recovered in enantiomerically enriched form. To achieve optimum enantiopurity of (1), such a process is ram until at least 50% substrate conversion is reached. Alternatively, the enzyme hydrolyses compound (1) selectively and the reaction is quenched before substrate conversion exceeds 50%. The resulting carboxylic acid is re-esterified to obtain compound (1) in enantiomerically enriched form. It will also be recognised by those skilled in the art that that such bioresolution processes can be adapted for operation in a non-hydrolytic mode, for example, in which a carboxylic acid undergoes enzymatic esterification or transesterification by reaction with an alcohol or ester, respectively.

The distinguishing feature of the present invention is use of an enzyme derived from a non-mammalian source. The non-mammalian source is typically a micro-organism, which can be a yeast, a fungus or a bacterium. The enzyme can be a wild type enzyme, a recombinant form of a wild type enzyme or genetically modified enzyme, each of which can provided in the form of a whole cell, a lyophilised whole cell, a cell-free enzyme preparation or an at least partially purified isolated enzyme, which may optionally be immobilised. Enzymes suitable for the process of the present invention are those exhibiting an E value of at least 5. Preferably, the enzyme will exhibit a higher E value, of at least 15 and more preferably of at least 30. Volume productivity in the process of the present invention is another important factor. The final product concentration accumulating in the reaction mixture is preferably at least 3 g/L. Preferably, the final product concentration is at least 5 g/L and more preferably at least 20 g/L.

In seeking to identify suitable enzymes, our approach has been to screen for catalysts of microbial origin from our microbe and enzyme collections. From an extensive search of approximately 150 yeasts and fungi and over 700 other micro-organisms, only two isolates capable of selectively hydrolysing the racemic ester (2) were identified. The recalcitrance of this substrate is highlighted by the fact we were unable to confirm any activity in esterases and lipases available on the open market and at our disposal, other than with PIE.

In one embodiment of the present invention, the non-mammalian source of the enzyme is a yeast, which may be selected from the genus *Rhodosporidium*, a preferred species being *Rhodosporidium toruloides*. These organisms have been shown to demonstrate the activity in a growth linked manner. Activity is optimum at around pH 8. Typically, processes enabled by such biocatalysts show around 60% conversion of substrate after overnight incubation at 25° C., in cases where initial substrate concentration is around 5 g/L, or higher. More specifically, the following strains of yeast contain one or more enzymes with esterase or lipase activity, which enables the preparation of ester (1) by enantioselective hydrolysis of the racemic ester (2):

The *Rhodosporidium toruloides* strain CMC 103105 deposited at NCIMB Limited on 28 Jul. 2004 and assigned the provisional accession number 41238;

The *Rhodosporidium toruloides* CMC 103107 deposited at NCIMB Limited on 28 Jul. 2004 and assigned the provisional accession number 41239.

In another embodiment of the present invention, the non-mammalian source of the enzyme is a fungus selected from the genus *Ophiostoma*. A preferred species is *Ophiostoma novo-ulmi*. Esterases obtained from such fungi have been demonstrated to have utility in the bioresolution of carboxylic esters for manufacture of profen drugs such as Naproxen and (S)-Ketoprofen. This is further described in U.S. Pat. No. 5,912,164, the contents of which are incorporated herein by reference.

The present invention is further illustrated by the following examples.

Example 1

Preparation of Organisms for Screening

Yeasts were grown in 100 ml of yeast malt extract broth in a 500 ml Erlenmeyer flask for 24-48 h at 25° C. They were harvested by centrifugation prior to resuspension in one-half of the original culture C in volume of 10% glycerol in phosphate buffered saline and stored at −80° C.

Example 2

Screening of Biocatalysts (Whole Cells and Isolated Enzymes)

Initial screening was performed using 5 g/l racemic methyl 5-chloro-2-isopropylpent-4-enoate in 0.1M phosphate buffer pH7+0.1% w/v tween 80. Typically 200 µl was added to the lyophilised cells from 0.5 ml of culture or of 1 mg of enzyme. Reactions were incubated for 2 days prior to dilution in acetonitrile and analysis by gas chromatography using a Chirasil dex CB column. *Rhodosporidium toruloides* CMC 103105 and *Rhodosporidium toruloides* CMC103107 were identified as having the desired activity, showing unreacted ester of 7% ee after 7-8% substrate conversion.

Example 3

Growth of Yeasts and Confirmation of Activity

Yeasts were grown from a glycerol stock in 100 mls of yeast malt extract broth contained within a 500 ml Erlenmeyer flask, at 25° C. Cells were harvested by centrifugation at 10,000 g. The pellet from 40 ml of culture was then resuspended in 5 ml phosphate buffered saline. 0.5 ml resuspended cells was added to 0.5 ml 5 g/l Synthon B in 0.1% tween 80 in phosphate buffered saline and incubated at 30° C., overnight. *Rhodosporidium toruloides* CMC 103105 was confirmed as having the desired activity, with single enantiomer (S)-methyl 5-chloro-2-isopropylpent-4-enoate being obtained after reaction overnight, with an apparent E value of 28. Similar reactions were performed to confirm the activity of the profen esterases described in U.S. Pat. No. 5,912,164. For this purpose, the growth medium for the recombinant *E. coli* was tryptone soya broth plus additions of isopropyl-beta-D-thiogalactopyranoside and ampicillin.

Example 4

Fermentation of *Rhodosporidium toruloides* CMC103105

Batch fermentation were performed at the 2 and 20l scale, both using yeast malt extract supplemented with 0.1% polypropylene glycol antifoam. No pH control was performed. A single vial of glycerol stock was used to inoculate 100 ml of YM broth. After 24 hours growth this was used to provide a 0.5% v/v inoculum to the fermenter. After 24 hours growth, cells were harvested by centrifugation and stored at −20° C. until required.

Example 5

Resolution of rac-methyl 5-chloro-2-isopropylpent-4-enoate at Different Concentrations of Substrate and Biocatalyst i) (S)-Methyl 5-chloro-2-isopropylpent-4-enoate was obtained in >99% ee (GC analysis) by resolution of rac-methyl 5-chloro-2-isopropylpent-4-enoate at a concentration of 8 g/l on reaction with frozen cells of *Rhodosporidium toruloides* CMC103105 at a concentration of 5% w/v after 24 hours. The E value for the reaction was calculated as 41.3. The reaction buffer for this reaction was Tris-HCl (0.1 M, pH 8.0). The reaction pH was maintained at pH 8.0 by the addition of aqueous sodium hydroxide (1 M). The reaction was performed at 21° C. with vigorous stirring.

ii) (S)-Methyl 5-chloro-2-isopropylpent-4-enoate was obtained in >99% ee (GC analysis) by resolution of rac-methyl 5-chloro-2-isopropylpent-4-enoate at a concentration of 15 g/l was achieved after 18 hours with frozen cells of *Rhodosporidium toruloides* CMC3105 at a loading of 15% w/v. The E value for the reaction was calculated as 23. The reaction buffer was Tris-HCl (0.1 M, pH 8.0). The reaction pH was maintained at pH 8.0 by the addition of aqueous sodium hydroxide (1 M). The reaction was performed at 21° C. with vigorous stirring.

iii) (S)-Methyl 5-chloro-2-isopropylpent-4-enoate was obtained in >99% ee (GC analysis) by resolution of rac-methyl 5-chloro-2-isopropylpent-4-enoate at a concentration of 50 g/l on reaction with frozen cells of *Rhodosporidium toruloides* CMC3105 (15% w/v) after 95 hours. The reaction buffer was Tris-HCl (0.1 M, pH 8.0). The reaction pH was maintained at pH 8.0 by the addition of aqueous sodium hydroxide (1 M). The reaction was performed at 21° C. with vigorous stirring.

Example 6

Preparative Scale Resolution of rac-methyl 5-chloro-2-isopropylpent-4-enoate To a stirred mixture of rac-methyl 5-chloro-2-isopropylpent-4-enoate (80.0 g, 0.41 mol) and 0.1M Tris.HCl pH 8.0 (9.4 L) at 20° C., frozen cells of *Rhodosporidium toruloides* CMC103105 (620 g) were added. The reaction pH was maintained at 8.0 by the addition of 1.0M NaOH. When the enantiomeric excess of the residual S-isomer was determined by GC to be >98%, the reaction was stopped by acidification to pH 2.5 with 6M HCl and centrifugation at 15000 g. The resultant cell pellet was resuspended in MeCN (1.5 L), stirred for 30 minutes, and filtered through celite. The filtrate was concentrated in vacuo and redissolved in MTBE (1 L). This solution was washed with saturated aq. $NaHCO_3$ (2×750 mL). The organic phases were combined and washed with saturated brine (500 mL). After washing of the brine with $CH_2Cl_2$ (500 mL), all the organic phases were combined, dried with $MgSO_4$ and concentrated in vacuo to yield a brown oil, which could be decolourised by refluxing in the presence of activated carbon (7.5 g) in MTBE (250 mL). After cooling and filtration through celite, concentration in vacuo gave a pale yellow oil (33.37 g). NMR revealed this material to contain approximately 15% carboxylic acid. This was removed by redissolution in MTBE (250 mL) and washing with saturated aq. $NaHCO_3$ (3×125 mL). Drying of the organic phase ($MgSO_4$) and concentration in vacuo gave (S)-methyl 5-chloro-2-isopropylpent-4-enoate as a pale yellow oil (27.38 g, 34% yield). This material was twice distilled under vacuum to produce a sample of (S)-methyl 5-chloro-2-isopropylpent-4-enoate as a colourless oil (11.60 g, ee 99.3%, 98.4% purity).

Example 7

Comparison of *Ophiostoma* Esterases

Growth and activity determination of a series of recombinant *Ophiostoma* related esterases was performed as in Example 3. Three related enzymes were shown to demonstrate varying ability to selectivity hydrolyse racemic ester (2); including a recombinant Ketoprofen esterase CMC104131 (E=4.31 with 23% conversion in 24 hours), Naproxen esterase CMC104432 (E=1.1 with 45% conversion 24 hours) and the previously described *Aspergillus tamarii* CMC104383 (WO 9904015) inactive. These three esterases demonstrate markedly different selectivities yet differ by only three amino acids.

The invention claimed is:

1. A process for preparing a compound of formula (1) in enantiomerically enriched form, which comprises selective hydrolysis of the corresponding racemic compound (2) catalysed by an enzyme derived from a non-mammalian source and having esterase or lipase activity, wherein R is methyl or $C_{2-10}$ linear or branched alkyl

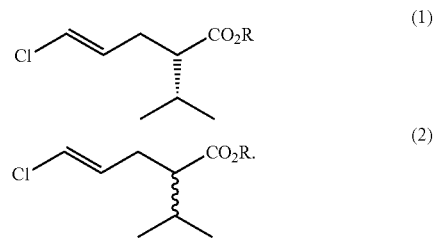

2. A process according to claim 1, wherein R is methyl or $C_{2-6}$ linear alkyl.

3. A process according to claim 2, wherein R is methyl or ethyl.

4. A process according to claim 1, wherein the enzyme hydrolyses the opposite of enantiomer of compound (1) selectively, and unreacted compound (1) is recovered in enantiomerically enriched form.

5. A process according to claim 1, wherein the enzyme hydrolyses compound (1) selectively, and the resulting carboxylic acid is re-esterified to obtain compound (1) in enantiomerically enriched form.

6. A process according to claim 1, wherein the enzyme is a wild type enzyme, a recombinant form of a wild type enzyme or a genetically modified enzyme.

7. A process according to claim 1, wherein the enzyme is provided in the form of a whole cell, a lyophilised whole cell, a cell-free enzyme preparation or an at least partially purified isolated enzyme, which may optionally be immobilised.

8. A process according to claim 1, wherein the non-mammalian source is a microorganism selected from the group consisting of yeasts, fungi and bacteria.

9. A process according to claim 8, wherein the non-mammalian source is a yeast from the genus *Rhodosporidium*.

10. A process according to claim 9, wherein the yeast is *Rhodosporidium toruloides*.

11. A process according to claim 10, wherein the yeast is *Rhodosporidium toruloides* CMC 103105 or CMC 103107.

12. A process according to claim 1, wherein enantioselectivity corresponding to an E value of at least 5 is achieved.

13. A process according to claim 1, wherein enantioselectivity corresponding to an E value of at least 15 is achieved.

14. A process according to claim 1, wherein the final product concentration is at least 3 g/l.

15. A process according to claim 1, wherein the final product concentration is at least 5 g/l.

16. A process according to claim 1, wherein the final product concentration is at least 20 g/l.

17. A process according to claim 1, wherein an enzyme is in the form of a whole cell derived from wild type yeast *Rhodosporidium toruloides* CMC 103105.

* * * * *